United States Patent
Hu et al.

(10) Patent No.: US 12,234,481 B2
(45) Date of Patent: Feb. 25, 2025

(54) USE OF EXOSOME DERIVED FROM DECIDUAL NATURAL KILLER (DNK) CELLS OR DNK CELL SUBSET IN PREPARATION OF DRUG AND AUXILIARY THERAPEUTIC AGENT FOR INFERTILITY-RELATED DISEASES

(71) Applicant: PHARCHOICE THERAPEUTICS INC, Shanghai (CN)

(72) Inventors: Shi Hu, Shanghai (CN); Min Ding, Shanghai (CN)

(73) Assignee: PHARCHOICE THERAPEUTICS INC, Shanghai (CN)

( * ) Notice: Subject to any disclaimer, the term of this patent is extended or adjusted under 35 U.S.C. 154(b) by 774 days.

(21) Appl. No.: 17/426,120

(22) PCT Filed: Sep. 30, 2020

(86) PCT No.: PCT/CN2020/119327
§ 371 (c)(1),
(2) Date: Jul. 28, 2021

(87) PCT Pub. No.: WO2021/103817
PCT Pub. Date: Jun. 3, 2021

(65) Prior Publication Data
US 2022/0096550 A1    Mar. 31, 2022

(30) Foreign Application Priority Data
Nov. 27, 2019    (CN) .......................... 201911178817.7

(51) Int. Cl.
A61K 35/17    (2015.01)
A61P 15/08    (2006.01)
C12N 5/0783   (2010.01)

(52) U.S. Cl.
CPC ............ *C12N 5/0646* (2013.01); *A61K 35/17* (2013.01); *A61P 15/08* (2018.01); *C12N 2509/00* (2013.01)

(58) Field of Classification Search
CPC .................................................. C12N 5/0646
See application file for complete search history.

(56) References Cited

U.S. PATENT DOCUMENTS

| | | |
|---|---|---|
| 2013/0195899 A1 | 8/2013 | Ichim et al. |
| 2018/0064425 A1 | 3/2018 | Sanyal |
| 2018/0369351 A1 | 12/2018 | Ichim et al. |

FOREIGN PATENT DOCUMENTS

| | | |
|---|---|---|
| CN | 107998149 A | 5/2018 |
| CN | 108815189 A | 11/2018 |
| CN | 109908180 A | 6/2019 |
| CN | 110721196 A | 1/2020 |
| CN | 110946878 A | 4/2020 |

OTHER PUBLICATIONS

Neviani et al, Natural Killer-Derived Exosomal miR-186 Inhibits Neuroblastoma Growth and Immune Escape Mechanisms. Cancer research, (20190315) vol. 79, No. 6, pp. 1151-1164 (Year: 2019).*
Yang Hong, et al., Research Progress of Endometrial Cell Exosome, J Int Obstet Gynecol, 2018, pp. 574-578, vol. 45 No. 5.
David W. Greening, et al., Human Endometrial Exosomes Contain Hormone-Specific Cargo Modulating Trophoblast Adhesive Capacity: Insights into Endometrial-Embryo Interactions, Biology of Reproduction, 2016, pp. 1-15, 94(2):38.
Noble K. Kurian, et al., Extracellular vesicle mediated embryo-endometrial cross talk during implantation and in pregnancy, Journal of Assisted Reproduction and Genetics, 2019, pp. 189-198, vol. 36.
Zeinab Latifi, et al., Potential roles of metalloproteinases of endometrium-derived exosomes in embryo-maternal crosstalk during implantation, Journal of Cellular Physiology, 2017.
Mian Liu, et al., Decidual small extracellular vesicles induce trophoblast invasion by upregulating N-cadherin, Reproduction, 2020, pp. 171-180, vol. 159.
York Hunt NG, et al., Endometrial Exosomes/Microvesicles in the Uterine Microenvironment: A New Paradigm for Embryo-Endometrial Cross Talk at Implantation, PLOS ONE, 2013, pp. 1-13, vol. 8 Issue 3, e58502.
Emily E. Hadley, et al., Amnion epithelial cell-derived exosomes induce inflammatory changes in uterine cells, American Journal of Obstetrics & Gynecology, 2018, 478.e1-478.e21, vol. 219.
Louise A. Koopman, et al., Human Decidual Natural Killer Cells Are a Unique NK Cell Subset with Immunomodulatory Potential, J. Exp. Med., 2003, pp. 1201-1212, vol. 198, No. 8.
Qun Zhang, et al., Decidual NK Cells and Their Secreted Cytokines and Pregnancy, Current Immunology, 2006, pp. 350-352, vol. 26 No. 4, Current Immunology.
Chunqing Li, et al., Research Progress on the Relationship Between Decidual NK Cells And Pregnancy, Prog Obstet Cynecol, 2016, pp. 378-380, vol. 25 No. 5.
Ying Xiang, et al., Decidual macrophages modulate trophoblast cells by transferring exo-somes in unexplained recurrent spontaneous abortion, Chinese Journal of Pathophysiology, 2019, pp. 1706-1709, 1728, vol. 35 No. 9.

(Continued)

*Primary Examiner* — Qiuwen Mi
(74) *Attorney, Agent, or Firm* — Bayramoglu Law Offices LLC

(57) ABSTRACT

Use of an exosome derived from decidual natural killer (dNK) cells or a dNK cell subset in the preparation of a drug and an auxiliary therapeutic agent for infertility-related diseases is provided. Experiments have confirmed that the exosome treats the endometrial growth disorder-related diseases by promoting increase of endometrial thickness, increasing endometrial cell viability, reducing endometrial cell damage, promoting VEGF expression, and maintaining stemness and stimulating proliferation of endometrial stromal cells, such that a conception rate for endometrial injury model mice increases from 20% to 50%-70%; and the exosome treats the maternal-fetal immune tolerance disorder-related diseases by exerting immune tolerance, reducing a spontaneous abortion rate, and increasing a helper T cell level. In addition, the exosome effectively increases the development rate of eggs fertilized in vivo or in vitro in a multiplying way, and improves an implantation rate and a birth rate for in vitro fertilization and embryo transfer.

10 Claims, No Drawings

(56) References Cited

OTHER PUBLICATIONS

Dong Xiao-Xiao, et al., The Significance of Exosomes in the Development, Diagnosis and Treatment of Endometriosis, J Int Obstet Gynecol, 2018, pp. 283-286, vol. 45 No. 3.

Dandan Li, et al., Genome-wide identification of microRNAs in decidual natural killer cells from patients with unexplained recurrent spontaneous abortion, Am J Reprod Immunol., 2018, pp. 1-9, e13052.

Du Jihui, et al. Expression patterns of NK cell subset in the decidua from unexplained recurrent spontaneous abortion, Int J Lab Med, 2012, pp. 2865-2866, vol. 33 No. 23.

Binqing Fu, et al., Natural Killer Cells Promote Fetal Development through the Secretion of Growth-Promoting Factors, Immunity, 2017, pp. 1100-1113, vol. 47.

Hong-Lin Jiang, et al., SSBP1 Suppresses TGF-β-Driven Epithelial-to-Mesenchymal Transition and Metastasis in Triple-Negative Breast Cancer by Regulating Mitochondrial Retrograde Signaling, Cancer Research, 2015, pp. 1-40, vol. 76 No. 4.

Pei-Fen Guo, et al., Thymic stromal lymphopoietin from trophoblasts induces dendritic cell-mediated regulatory TH2 bias in the decidua during early gestation in humans, Blood, 2010, pp. 2061-2069, vol. 116 No. 12.

Sandra M Blois, et al., A pivotal role for galectin-1 in fetomaternal tolerance, Nature Medicine, 2007, pp. 1450-1457, vol. 13 No. 12.

Byung-Ju Kim, et al., Seminal CD38 is a pivotal regulator for fetomaternal tolerance, PNAS, 2015, pp. 1559-1564, vol. 112 No. 5.

* cited by examiner

USE OF EXOSOME DERIVED FROM DECIDUAL NATURAL KILLER (DNK) CELLS OR DNK CELL SUBSET IN PREPARATION OF DRUG AND AUXILIARY THERAPEUTIC AGENT FOR INFERTILITY-RELATED DISEASES

CROSS REFERENCE TO THE RELATED APPLICATIONS

This application is the national phase entry of International Application No. PCT/CN2020/119327, filed on Sep. 30, 2020, which is based upon and claims priority to Chinese Patent Application No. 201911178817.7, filed on Nov. 27, 2019, the entire contents of which are incorporated herein by reference.

TECHNICAL FIELD

The present disclosure belongs to the field of biomedicine, and relates to use of an exosome derived from decidual natural killer (dNK) cells or a dNK cell subset in a preparation of a drug and an auxiliary therapeutic agent for infertility-related diseases, a preparation method of the exosome, and a pharmaceutical composition including the exosome.

BACKGROUND

Endometrial injury mainly refers to injury of a basal layer of endometrium, which is mostly related to dilatation and curettage during pregnancy. Compared with the normal endometrium, a basal layer of the endometrium during pregnancy is loose and more susceptible to injury. Based on the national conditions and the increasingly-high induced abortion rate in China, the occurrence of endometrial injury cannot be ignored. Injury of a basal layer of endometrium may lead to injury or loss of endometrial stem cells. Moreover, local infection and aseptic inflammation of damaged endometrium will destroy the niche microenvironment of stem cells, cause the regeneration and repair disfunction of epithelial and mesenchymal cells, block the angiogenesis, and lead to the formation of dense fibrous tissues. As a result, a uterine cavity is covered only with a small amount of endometrium or even without endometrium, glands undergo atrophy, and a uterine cavity loses the normal shape and function. Furthermore, immunologic disorders in a uterine cavity further mediate the risk of endometrial immunological abortion.

NK cells are a type of innate immune cells in endometrium. In early pregnancy, NK cells account for 40% to 70% of the total lymphocytes in decidua, which are a type of lymphocytes with a high content in normal decidua. Modern reproductive medicine studies show that human dNK cells have a unique phenotype of $CD56^{bright}CD16^-KIR^+CD49a^+$, which are different from peripheral NK cells and have almost no cytotoxicity. dNK cells locally participate in the promotion of angiogenesis, tissue remodeling, immune regulation, and placenta formation in the decidual tissue.

Recent hotspot research shows that viable cells can secrete a large number of exosomes, and the exosomes are formed by the following process: multivesicular endosomes (MVEs) are formed by the reverse budding of endosomes, then fused with a cell membrane, and released outside cells to form the exosomes. Almost all cells can secrete exosomes. These exosomes have a diameter of 30 nm to 150 nm and a density of 1.13 g/mL to 1.19 g/mL; express specific proteins that carry important signaling molecules of parent cells, including proteins, lipids, RNA, and the like; and retain the similar biological activities to parent cells.

According to existing research, there is no disclosure or suggestion of a function of dNK cell-derived exosomes, and there is no disclosure or suggestion of a technical solution to treat a disease using a product prepared from a dNK cell-derived exosome, which are unknown and need to be confirmed. Moreover, the dNK cell population refers to NK cells in the decidual tissue that have extremely-high heterogeneity and a phenotype of $CD56^{bright}CD16^-KIR^+CD9^+CD49a^+$, and the dNK cells can also be divided into many subsets with different functions according to the different expression of surface markers. In the prior art, there is no disclosure or suggestion of a technical solution to treat a disease using a product prepared from a specific marker-expressing dNK cell subset-derived exosome.

SUMMARY

In order to solve the above technical problems, the present disclosure provides use and a preparation method of a dNK cell-derived exosome, and a pharmaceutical composition including the exosome.

In a first aspect, the present disclosure provides use of an exosome derived from dNK cells or a dNK cell subset in the preparation of a drug and an auxiliary therapeutic agent for infertility-related diseases.

The dNK cells of the present disclosure have a surface marker of $CD56^{bright}CD16^-CD49a^+$, and the dNK cell subset refers to dNK cells with a surface marker that is any one or a combination of more from the group consisting of $CD39^+$, $CD27^+$, $CD160^+$, and $TIGIT^+$.

The dNK cell-derived exosome has a diameter of about 30 nm to 150 nm, and includes a lipid membrane enveloping protein and genetic materials such as mRNA and microRNA, and the exosome is obtained by enrichment through in vitro cultivation of isolated dNK cells or a specific marker-expressing dNK cell subset.

The infertility-related diseases may include endometrial growth disorder-related diseases and maternal-fetal immune tolerance disorder-related diseases. The endometrial growth disorder-related diseases may include endometrial injury, premature ovarian failure (POF), sexual hormone disturbance, polycystic ovarian syndrome (PCOS), pelvic inflammatory disease (PID), endometrial receptivity decline, endometritis, endometrial polyp, intrauterine adhesion (IUA), endometrial gland reduction, endometrial fibrosis, amenorrhoea, abnormal uterine bleeding (AUB), adenomyosis and endometriosis, reproductive tract infection, hysteromyoma, etc.; and the maternal-fetal immune tolerance disorder-related diseases may include recurrent spontaneous abortion, threatened abortion, assisted reproductive technology (ART) treatment failure, etc.

Therefore, the drug for treating infertility-related diseases may mainly include a drug for treating endometrial growth disorder-related diseases or a drug for treating maternal-fetal immune tolerance disorder-related diseases.

Specifically, the drug for treating endometrial growth disorder-related diseases may be any one or a combination of more from the group consisting of a drug for promoting increase of endometrial thickness, a drug for enhancing endometrial cell viability, a drug for reducing endometrial cell damage, a drug for promoting vascular endothelial growth factor (VEGF) expression, and a drug for maintaining stemness and stimulating proliferation of endometrial stromal cells. The drug for treating maternal-fetal immune tolerance disorder-related diseases may be any one or a combination of more from the group consisting of a drug for exerting immune tolerance, a drug for treating spontaneous abortion, and a drug for increasing a helper T cell level.

The auxiliary therapeutic agent for infertility-related diseases may be an agent composition for improving the normal development rate of fertilized eggs, which may be an agent for promoting the development and maturation of fertilized eggs or blastocysts, or a fertilized egg medium or in vitro fertilization medium that includes the exosome.

The agent for promoting the development and maturation of fertilized eggs or blastocysts may preferably be used in a fertilized egg medium to increase a development rate of fertilized eggs. The agent is administered orally, sublingually, subcutaneously, intravenously, intramuscularly, nasally, follicularly, or vaginally to a human or non-human animal mother with eggs. Compared with the case where the composition for improving a development rate of the present disclosure is not used, when the composition of the present disclosure is used, the normal development rate of fertilized eggs is significantly improved, and a conception rate is also improved. The composition can also be added to a medium for in vitro maturation of collected eggs, an egg cryopreservation agent, and so on.

The animal fertilized egg medium or in vitro fertilization medium that includes the exosome is not particularly limited, and a medium capable of cultivating mammalian fertilized eggs may be used, such as HTF medium, m-HTF medium, Ham medium, Ham F-10 medium, MEM medium, 199 medium, BME medium, CMRL1066 medium, McCoy-5A medium, Weymouth medium, TrowellT-8 medium, Leibovitz L-15 medium, NCTC medium, William-E medium, Kane and Foote medium, Brinster medium, m-Tyrode medium, BWW medium, WK Whitten medium, TYH medium, Hoppes & Pitts medium, m-KRB medium, BO medium, T6 medium, GPM medium, KSOM medium, HECM medium, and modified media of these media. Commercially-available special in vitro fertilization media such as mouse in vitro fertilization medium CARD MEDIUM and porcine embryo development and cultivation medium (PZM-5) may also be used.

In a second aspect, the present disclosure provides a preparation method of the dNK cell-derived exosome, including the following step:

A. Isolation of dNK Cells and dNK Cell Subsets
  (i) isolation of decidual tissue cells: digesting a decidual tissue with collagenase IV (Sigma-Aldrich) and DNase I (Shanghai Sangon) to obtain a cell suspension;
  (ii) isolation of lymphocytes: isolating lymphocytes through Percoll (GE Healthcare) density gradient centrifugation;
  (iii) isolation of dNK cells by flow cytometry (FCM): removing some impurity cells by a general technology, and conducting FCM or a magnetic bead method with anti-CD56 antibody, anti-CD16 antibody, and anti-CD49a antibody to isolate dNK cells, where the dNK cells have a marker of $CD56^{bright}CD16^-CD49a^+$;
  (iv) as needed, further conducting FCM or a magnetic bead method with anti-CD39 antibody, anti-CD27 antibody, anti-CD160 antibody, and anti-TIGIT antibody to isolate dNK cell subsets, where the dNK cell subsets have a marker that is any one and/or a combination of at least two from the group consisting of $CD39^+$, $CD27^+$, $CD160^+$, and $TIGIT^+$.

B. NK Cell Cultivation In Vitro
  transferring the NK cells or cell subsets to CTS AIM-V medium, 1640 medium, or DMEM medium that is free of serum, and cultivating at 37° C. and 5% $CO_2$ for 24 h to 96 h, where the medium generally does not include serum;

C. Isolation of the Exosome
  filtering a liquid culture obtained in step B through a 0.45 μm filter membrane, and subjecting a resulting filtrate successively to centrifugation at 4° C. and 1,000 g for 10 min, centrifugation at 4° C. and 2,000 g for 20 min, centrifugation at 4° C. and 10,000 g for 30 min, and centrifugation at 110,000 g for 90 min; discarding a resulting supernatant, and resuspending a resulting precipitate with phosphate buffered saline (PBS); subjecting a resulting suspension once again to centrifugation at 110,000 g for 90 min, discarding a resulting supernatant, and resuspending a resulting precipitate with a small amount of PBS; and filtering a resulting suspension through a 0.45 μm filter membrane to obtain the exosome.

In a third aspect, the present disclosure provides a pharmaceutical composition for infertility-related diseases, and the pharmaceutical composition is composed of a dNK cell-derived exosome and a pharmaceutically acceptable adjuvant. The exosome is the main or even the only active ingredient in the pharmaceutical composition. The adjuvant helps the exosome to exert its curative effect more stably. The preparation can ensure the conformational integrity of the exosome disclosed in the present disclosure, and also protect active functional groups in the exosome from degradation.

Normally, a liquid preparation can be stored at 2° C. to 8° C. for at least three months, and a lyophilized preparation can be stored at −30° C. for at least six months.

In terms of dosage form, the pharmaceutical composition may be a tablet, a pill, a powder, an injection, a tincture, a solution, an extract, an ointment, and other dosage forms commonly used in the pharmaceutical field; may also be a preparation for uterine mucosal administration, such as a film, a suppository, a tablet, an effervescent tablet, a gel, and an intrauterine drug delivery system such as a stent; and may also be a mucosal absorption enhancer, such as a surfactant, a chelating agent, a fatty acid, a fatty alcohol, a fatty acid ester, a cyclodextrin derivative, and a protease inhibitor.

Similar to the use of the exosome, the present disclosure also provides use of the pharmaceutical composition in the preparation of a product for treating and preventing infertility-related diseases. An effective amount of the exosome and/or composition can be administered to a subject (human or animal) with an infertility-related disease, and can also be administered prophylactically to a healthy subject at risk of infertility.

In a fourth aspect, the present disclosure provides an auxiliary therapeutic agent for infertility-related diseases, and the auxiliary therapeutic agent is composed of a dNK cell-derived exosome and a pharmaceutically acceptable adjuvant, or is an animal fertilized egg medium or in vitro fertilization medium that includes the exosome.

Preferably, in the auxiliary therapeutic agent, a mass-to-volume ratio of the exosome may be 0.02% (a mass of the exosome refers to a mass of protein in the exosome) or other values, provided that the normal development rate of fertilized eggs can be improved, which is not particularly limited.

In a fifth aspect, the present disclosure provides a kit for improving the normal development rate of fertilized eggs that can be used for development in vitro or in vivo. The present disclosure has no specific limitations on the kit, provided that the kit includes the exosome as an active ingredient. A kit that further includes one or more in vitro culture media of mammalian fertilized eggs may be used.

Compared with the prior art, the present disclosure has the following technical effects:

The present disclosure provides use of an exosome derived from dNK cells or a dNK cell subset in the preparation of a drug and an auxiliary therapeutic agent for infertility-related diseases. Experiments have confirmed that the exosome treats the endometrial growth disorder-related diseases by promoting increase of endometrial thickness, enhancing endometrial cell viability, reducing endometrial cell damage, promoting VEGF expression, and maintaining stemness and stimulating proliferation of endometrial stromal cells, such that a conception rate for endometrial injury model mice increases from 20% to 50%-70%; and the exosome treats the maternal-fetal immune tolerance disorder-related diseases by exerting immune tolerance, reducing a spontaneous abortion rate, and increasing a helper T cell level.

In addition, the exosome of the present disclosure can effectively increase the development rate of eggs fertilized in vivo or in vitro in a multiplying way, and also can improve an implantation rate and a birth rate for in vitro fertilization and embryo transfer, which plays an active auxiliary role in the treatment of infertility.

Therefore, the exosome of the present disclosure can not only show a specified therapeutic or alleviating effect on infertility-related diseases, but also play an active auxiliary role by improving the normal development rate of fertilized eggs, which provides a new way for the treatment of infertility.

DETAILED DESCRIPTION OF THE EMBODIMENTS

The following examples and experimental examples are provided to further illustrate the present disclosure, and shall not be construed as a limitation to the present disclosure. Moreover, the examples do not include detailed descriptions of traditional methods.

Example 1

Screening of Candidate Markers for dNK Cells

In the statistical calculations in this example and the following examples, different statistical modes of the software SPSS 22.0 were selected to calculate the p value according to requirements for evaluation of the significance of differences between 2 groups, differences among 3 or more groups, or difference between ratios.

Decidual tissues were collected from 10 healthy cases undergoing early pregnancy termination due to non-medical reasons (normal group) and 5 cases undergoing early pregnancy termination due to spontaneous abortion (abortion group), and NK cells were isolated by fluorescence-activated cell sorting (FACS) with reference to the literature [Fu B, et al. Immunity, 2017, 47 (6): 1100-1113.e6.]. For example: The decidual tissue was digested with 1 mg/mL collagenase IV (Sigma-Aldrich) and 0.01 mg/mL DNase I (Shanghai Sangon) for 1 h, then lymphocytes were obtained by Percoll (GE Healthcare) density gradient centrifugation and then cultivated on a petri dish at 37° C. for 2 h to remove stromal cells and macrophages, and NK cells were isolated by FCM. The CD56 antibody, CD3 antibody, and CD14 antibody were first used to preliminarily sort out NK cells, and then the CD16 antibody and CD49a antibody were used to further sort out dNK cells, which were dNK cells with a phenotype of $CD56^{bright}CD16^-CD49a^+$ ($CD56^{bright}CD16^-CD49a^+CD3^-CD14^-$). NK cells obtained in the normal group and the abortion group were lysed, a protein concentration was determined by the Bradford method, and lysates of the two groups were subjected to protein expression analysis by the iTRAQ-nano-HPLC-MS/MS method, thus determining different membrane surface marker expression levels on the groups of NK cells. The methods could refer to the literature [Jiang, Hong-Lin, et al. Cancer research 76.4 (2016): 952-964.]. According to clustering statistical analysis of membrane surface markers, the expression of CD39 (UniProtKB: P49961), CD27 (UniProtKB: P26842), CD160 (UniProtKB: O95971), and TIGIT (UniProtKB: Q495A1) on dNK cells of the normal group was significantly higher than that on dNK cells of the abortion group.

Example 2

Preparation of dNK Cells and dNK Cell Subsets

A decidual tissue collected from a case undergoing early pregnancy termination due to non-medical reasons was used to prepare dNK cells, which was implemented according to the method described in Example 1. Briefly: The decidual tissue was digested with 1 mg/mL collagenase IV (Sigma-Aldrich) and 0.01 mg/mL DNase I (Shanghai Sangon) for 1 h, and then lymphocytes were obtained by Percoll (GE Healthcare) density gradient centrifugation. The lymphocytes were cultivated at 37° C. for 2 h on a petri dish to remove stromal cells and macrophages, and then NK cells were isolated by FCM. dNK cells with a phenotype of $CD56^{bright}CD16^-CD49a^+TIGIT^+$ were obtained. Antibody magnetic beads were used to further sort out $CD56^{bright}CD16^-CD49a^+CD39k$-positive dNK cell subset, $CD56^{bright}CD16^-CD49a^+CD27^+$-positive dNK cell subset, $CD56^{bright}CD16^-CD49a^+CD160^+$ dNK cell subset, $CD56^{bright}CD16^-CD49a^+TIGIT^+$-positive dNK cell subject, and $CD56^{bright}CD16^-CD49a^+CD39^+TIGIT^+$-positive dNK cell subset. The obtained cells could be directly tested, used, or cryopreserved. The peripheral blood was collected from the same volunteer, and NK cells were isolated according to the general method and used as control cells.

Example 3

Preparation of Exosomes Derived from dNK Cells and dNK Cell Subsets

The dNK cells and dNK cell subsets and control NK cells freshly isolated in Example 2 were cultivated in a serum-free 1640 medium for 24 h. The cells were removed by centrifugation, a culture supernatant was filtered through a 0.45 μm filter membrane and then centrifuged at 4° C. and 1,000 g for 10 min, and a resulting supernatant was collected; the collected supernatant was centrifuged at 4° C. and 2,000 g for 20 min, and a resulting supernatant was collected; the collected supernatant was centrifuged at 4° C. and 10,000 g for 30 min, and a resulting supernatant was collected; the collected supernatant was centrifuged at 110,000 g for 100 min, a resulting supernatant was discarded, and a resulting precipitate was resuspended with PBS; and a resulting suspension was centrifuged once again at 110,000 g for 100 min, a resulting supernatant was discarded, and a resulting precipitate was resuspended with a small amount of PBS and then filtered through a 0.45 μm filter membrane to obtain an exosome. The Bradford method was used to detect the total exosome protein (Bio-Rad Protein Assay Reagent). Obtained exosomes were lyophilized and stored at −80° C. The following six exosomes were obtained: $CD56^{bright}CD16^-CD49a^+$-positive dNK cell-derived exosome, $CD56^{bright}CD16^-CD49a^+CD39^+$-positive dNK cell-derived exosome, $CD56^{bright}CD16^-CD49a^+CD27^+$-positive dNK cell-derived exosome, $CD56^{bright}CD16^-CD49a^+CD160^+$-positive dNK cell-derived exosome, $CD56^{bright}CD16^-CD49a^+TIGIT^+$-positive dNK cell-derived exosome, and $CD56^{bright}CD16^-CD49a^+CD39^+TIGIT^+$-positive dNK cell-derived exosome. An exosome derived from the peripheral NK cells in Example 2 was used as a control exosome.

Example 4

Effects of the Exosomes to Enhance Endometrial Cell Viability, Reduce Endometrial Cell Damage, and Increase VEGF Expression Non-pathological endometrial stromal cells were cultivated for 24 h, and each of the exosomes obtained in Example 3 was added, where a ratio of a mass of the exosome protein to a volume of the medium matrix was 0.02% (that is, a relative mass-to-volume ratio). The control exosome in Example 3 was used in the control group, and no exosome was used in the blank group. After the treatment was conducted for 48 h, stromal cells and media were sampled for analysis.

The cell viability of the stromal cells was determined by the PrestoBlue method (Thermo Fisher Scientific), and the determination was conducted 48 h after the treatment. The value was expressed as an average value (%) obtained after normalization relative to the control (Table 1).

TABLE 1

Relative cell viability of stromal cells

| Group (exosome treatment group, 0.02%) | Average value | SD | p value |
|---|---|---|---|
| Blank (medium only) | 100.00 | 14.63 | |
| Control exosome | 101.66 | 4.55 | |
| $CD56^{bright}CD16^-CD49a^+$-positive dNK cell-derived exosome | 158.37 | 24.99 | $p < 0.05$ |
| $CD56^{bright}CD16^-CD49a^+CD39^+$-positive dNK cell subset-derived exosome | 140.49 | 8.32 | $p < 0.05$ |
| $CD56^{bright}CD16^-CD49a^+CD27^+$-positive dNK cell subset-derived exosome | 172.69 | 24.81 | $p < 0.05$ |
| $CD56^{bright}CD16^-CD49a^+CD160^+$-positive dNK cell subset-derived exosome | 159.90 | 11.93 | $p < 0.05$ |
| $CD56^{bright}CD16^-CD49a^+TIGIT^+$-positive dNK cell subset-derived exosome | 161.14 | 18.66 | $p < 0.05$ |
| $CD56^{bright}CD16^-CD49a^+CD39^+TIGIT^+$-positive dNK cell subset-derived exosome | 179.38 | 23.61 | $p < 0.05$ |

Conclusion: The exosomes derived from dNK cells and dNK cell subsets of the present disclosure have the ability to increase the uterine stromal cell viability, and can be used as a product for enhancing endometrial proliferation.

Further evaluation of a stromal cell damage level: A lactate dehydrogenase (LDH) detection kit was used to determine a cell damage level by colorimetry, such that cell damage could be quantified based on the determination of LDH activity in damaged cells in the medium. Increased cell membrane damage and cell lysis lead to an increase in LDH activity, which was proportional to the number of lysed cells. After the exosome treatment was conducted for 48 h, LDH activity was determined in the medium, and a value was expressed as an average value (%) obtained after normalization relative to the control (Table 2).

TABLE 2

LDH activity

| Group (exosome treatment group, 0.02%) | Average value | SD | p value |
|---|---|---|---|
| Blank (medium only) | 100.00 | 15.75 | |
| Control exosome | 103.35 | 7.65 | |
| $CD56^{bright}CD16^-CD49a^+$-positive dNK cell-derived exosome | 67.77 | 7.11 | $p < 0.05$ |
| $CD56^{bright}CD16^-CD49a^+CD39^+$-positive dNK cell subset-derived exosome | 63.54 | 7.64 | $p < 0.05$ |
| $CD56^{bright}CD16^-CD49a^+CD27^+$-positive dNK cell subset-derived exosome | 49.01 | 7.10 | $p < 0.05$ |
| $CD56^{bright}CD16^-CD49a^+CD160^+$-positive dNK cell subset-derived exosome | 36.12 | 5.86 | $p < 0.05$ |
| $CD56^{bright}CD16^-CD49a^+TIGIT^+$-positive dNK cell subset-derived exosome | 49.50 | 7.33 | $p < 0.05$ |
| $CD56^{bright}CD16^-CD49a^+CD39^+TIGIT^+$-positive dNK cell subset-derived exosome | 32.71 | 5.08 | $p < 0.05$ |

Conclusion: The exosomes derived from dNK cells and dNK cell subsets of the present disclosure have the ability to alleviate membrane damage, and can be used as a product for enhancing stromal cell viability.

The potential enhancement effect of the exosomes on the VEGF expression of endometrial stromal cells was further investigated. After the exosome treatment was conducted for 48 h, the VEGF concentration in the medium was determined by ELISA. Results were shown in Table 3.

TABLE 3

VEGF expression

| Group (exosome treatment group, 0.02%) | VEGF (pg/ml) | SD | p value |
|---|---|---|---|
| Blank (medium only) | 250.77 | 24.63 | |
| Control exosome | 244.36 | 20.55 | |
| $CD56^{bright}CD16^-CD49a^+$-positive dNK cell-derived exosome | 491.37 | 38.32 | $p < 0.05$ |
| $CD56^{bright}CD16^-CD49a^+CD39^+$-positive dNK cell subset-derived exosome | 666.51 | 42.20 | $p < 0.05$ |
| $CD56^{bright}CD16^-CD49a^+CD27^+$-positive dNK cell subset-derived exosome | 701.70 | 97.36 | $p < 0.05$ |
| $CD56^{bright}CD16^-CD49a^+CD160^+$-positive dNK cell subset-derived exosome | 998.65 | 55.49 | $p < 0.05$ |
| $CD56^{bright}CD16^-CD49a^+TIGIT^+$-positive dNK cell subset-derived exosome | 842.76 | 89.50 | $p < 0.05$ |
| $CD56^{bright}CD16^-CD49a^+CD39^+TIGIT^+$-positive dNK cell subset-derived exosome | 572.33 | 76.63 | $p < 0.05$ |

Conclusion: The exosomes derived from dNK cells and dNK cell subsets of the present disclosure can promote the expression of VEGF, which has the effect of enhancing endometrial angiogenesis.

Example 5

Promotion of the Exosomes on the Marker Expression on Endometrial Stromal Cells

Non-pathological endometrial stromal cells were cultivated for 24 h, and each of the exosomes obtained in Example 3 was added, where a ratio of a mass of the exosome protein to a volume of the medium matrix was 0.02% (that is, a relative mass-to-volume ratio). The control exosome in Example 3 was used in the control group. The stromal cells were further cultivated for 24 h in an incubator at 37° C. and 5% $CO_2$, and then the ALDH positive rate and Ki67 positive rate were determined for the stromal cells by FCM. Results were shown in Tables 4 and 5.

TABLE 4

ALDH positive rate

| Group (exosome treatment group, 0.02%) | ALDH positive rate | SD | p value |
|---|---|---|---|
| Blank (medium only) | 3.65 | 0.74 | |
| Control exosome | 3.15 | 0.66 | |
| $CD56^{bright}CD16^-CD49a^+$-positive dNK cell-derived exosome | 20.64 | 2.09 | p < 0.05 |
| $CD56^{bright}CD16^-CD49a^+CD39^+$-positive dNK cell subset-derived exosome | 28.15 | 2.87 | p < 0.05 |
| $CD56^{bright}CD16^-CD49a^+CD27^+$-positive dNK cell subset-derived exosome | 22.14 | 2.75 | p < 0.05 |
| $CD56^{bright}CD16^-CD49a^+CD160^+$-positive dNK cell subset-derived exosome | 30.45 | 4.31 | p < 0.05 |
| $CD56^{bright}CD16^-CD49a^+TIGIT^+$-positive dNK cell subset-derived exosome | 20.76 | 3.21 | p < 0.05 |
| $CD56^{bright}CD16^-CD49a^+CD39^+TIGIT^+$-positive dNK cell subset-derived exosome | 21.24 | 2.39 | p < 0.05 |

TABLE 5

Ki67 positive rate

| Group (exosome treatment group, 0.02%) | K167 positive rate | SD | p value |
|---|---|---|---|
| Blank (medium only) | 13.38 | 1.83 | |
| Control exosome | 12.57 | 2.15 | |
| $CD56^{bright}CD16^-CD49a^+$-positive dNK cell-derived exosome | 37.20 | 5.92 | p < 0.05 |
| $CD56^{bright}CD16^-CD49a^+CD39^+$-positive dNK cell subset-derived exosome | 38.63 | 5.50 | p < 0.05 |
| $CD56^{bright}CD16^-CD49a^+CD27^+$-positive dNK cell subset-derived exosome | 44.29 | 3.17 | p < 0.05 |
| $CD56^{bright}CD16^-CD49a^+CD160^+$-positive dNK cell subset-derived exosome | 42.34 | 3.89 | p < 0.05 |
| $CD56^{bright}CD16^-CD49a^+TIGIT^+$-positive dNK cell subset-derived exosome | 38.63 | 5.50 | p < 0.05 |
| $CD56^{bright}CD16^-CD49a^+CD39^+TIGIT^+$-positive dNK cell subset-derived exosome | 46.47 | 2.75 | p < 0.05 |

The results show that the exosomes derived from dNK cells and dNK cell subsets of the present disclosure have a very strong ability to maintain stemness and stimulate proliferation of stromal cells.

Example 6

Treatment of Endometrial Injury with the Exosomes

Patients had an endometrial thickness of less than 8 mm due to induced abortion, dilatation and curettage, infection, and other factors, which was clinically diagnosed as thin endometrium. Anti-infection and other treatments were given to the patients, which showed no effects. The patients were administered with a composition with the exosomes (exosomes derived from dNK cells and dNK cell subsets) prepared in Example 3 as an active ingredient at a dosage of 10 mg/kg. The composition could be administered by intravenous infusion or intrauterine perfusion, for example. The composition was administered to the patient one or more times to promote the increase in endometrial thickness.

Example 7

Effect of the Exosomes on Decidual Dendritic Cells (dDCs)

A decidual tissue was collected from a person undergoing pregnancy termination due to non-medical reasons, and DCs (CD1c positive) were isolated and sorted with reference to the literature (Guo P F, et al. Blood, 2010, 116 (12): 2061-2069). The DC cells were divided into a negative control group (treated with the control exosome described in Example 3, at a mass-to-volume ratio of 0.02%), treatment groups (treated with the exosomes derived from dNK cells and dNK cell subsets described in Example 3, at a mass-to-volume ratio of 0.02%), an LPS treatment group (100 ng/ml), and a blank group (without exosome). After the cells were cultivated for 48 h, the interleukin 10 (IL-10) and tumor necrosis factor α (TNF α) levels in a cultivation system were detected by methods described in the literature (Guo P F, et al. Blood, 2010, 116 (12): 2061-2069). Results showed that the exosomes significantly increased the IL-10 level, but did not increase the TNFα level (Tables 6 and 7). These results further confirmed that the exosomes derived from dNK cells and dNK cell subsets could exert immune tolerance through DCs.

TABLE 6

IL-10 content

| Group (exosome treatment group, 0.02%) | IL-10 (pg/ml) | SD | p value |
|---|---|---|---|
| Blank (medium only) | 45.08 | 4.35 | |
| Control exosome | 49.55 | 5.15 | |
| $CD56^{bright}CD16^-CD49a^+$-positive dNK cell-derived exosome | 542.79 | 84.21 | p < 0.05 |
| $CD56^{bright}CD16^-CD49a^+CD39^+$-positive dNK cell subset-derived exosome | 520.54 | 73.93 | p < 0.05 |
| $CD56^{bright}CD16^-CD49a^+CD27^+$-positive dNK cell subset-derived exosome | 500.95 | 34.03 | p < 0.05 |
| $CD56^{bright}CD16^-CD49a^+CD160^+$-positive dNK cell subset-derived exosome | 595.84 | 95.13 | p < 0.05 |
| $CD56^{bright}CD16^-CD49a^+TIGIT^+$-positive dNK cell subset-derived exosome | 483.63 | 35.80 | p < 0.05 |
| $CD56^{bright}CD16^-CD49a^+CD39^+TIGIT^+$-positive dNK cell subset-derived exosome | 496.95 | 63.74 | p < 0.05 |
| LPS | 391.75 | 47.56 | p < 0.05 |

TABLE 7

TNFα content

| Group (exosome treatment group, 0.02%) | TNFα (pg/ml) | SD | p value |
|---|---|---|---|
| Blank (medium only) | 27.76 | 3.43 | |
| Control exosome | 36.55 | 4.11 | |
| $CD56^{bright}CD16^-CD49a^+$-positive dNK cell-derived exosome | 13.82 | 1.17 | p > 0.05 |
| $CD56^{bright}CD16^-CD49a^+CD39^+$-positive dNK cell subset-derived exosome | 39.36 | 4.39 | p > 0.05 |
| $CD56^{bright}CD16^-CD49a^+CD27^+$-positive dNK cell subset-derived exosome | 32.11 | 4.73 | p > 0.05 |
| $CD56^{bright}CD16^-CD49a^+CD160^+$-positive dNK cell subset-derived exosome | 35.87 | 4.20 | p > 0.05 |

TABLE 7-continued

TNFα content

| Group (exosome treatment group, 0.02%) | TNFα (pg/ml) | SD | p value |
|---|---|---|---|
| CD56$^{bright}$CD16$^-$CD49a$^+$TIGIT$^+$-positive dNK cell subset-derived exosome | 21.14 | 2.99 | p > 0.05 |
| CD56$^{bright}$CD16$^-$CD49a$^+$CD39$^+$TIGIT$^+$-positive dNK cell subset-derived exosome | 32.83 | 2.33 | p > 0.05 |
| LPS | 1222.67 | 62.50 | p < 0.05 |

Example 8

Therapeutic Effect of the Exosomes on Spontaneous Abortion Models

CBA/J female mice and DBA/2J male mice were used to establish stress abortion models, which were classic research models for maternal-fetal immune tolerance disorders. The establishment method, experimental method, and observation time points could be seen in the literature (Blois S M, et al. Nature Medicine, 2007, 13 (12): 1450-1457). CBA/J female mice were divided into a negative control group, a stress group, a control group, and treatment groups before being raised together. The treatment groups were intravenously administered with the exosomes derived from dNK cells and dNK cell subsets of the present disclosure (150 μg/mouse) once every 3 days, with a total of 3 administrations. The control group was administered with the control exosome at the same dosage in the same administration route. The mice were raised together 3 days after the first administration. The mice were raised separately immediately after the pregnancy was determined by vaginal plug (effective n=10).

The experimental results (Table 8) showed that the abortion rate of the treatment group was significantly lower than that of the stress abortion group, indicating that the exosomes derived from dNK cells and dNK cell subsets have prominent therapeutic effects.

TABLE 8

Analysis of embryo absorption rate (abortion) of mice in each group

| Group | Embryo absorption rate | SD | p value (relative to stress + control cells) |
|---|---|---|---|
| Blank control group | 9.46 | 9.41 | |
| Stress + control exosome | 38.81 | 9.92 | |
| CD56$^{bright}$CD16$^-$CD49a$^+$-positive dNK cell-derived exosome | 13.76 | 14.36 | p < 0.05 |
| CD56$^{bright}$CD16$^-$CD49a$^+$CD39$^+$-positive dNK cell subset-derived exosome | 12.38 | 10.27 | p < 0.05 |
| CD56$^{bright}$CD16$^-$CD49a$^+$CD27$^+$-positive dNK cell subset-derived exosome | 17.30 | 9.03 | p < 0.05 |
| CD56$^{bright}$CD16$^-$CD49a$^+$CD160$^+$-positive dNK cell subset-derived exosome | 8.04 | 9.12 | p < 0.05 |
| CD56$^{bright}$CD16$^-$CD49a$^+$TIGIT$^+$-positive dNK cell subset-derived exosome | 12.86 | 10.96 | p < 0.05 |
| CD56$^{bright}$CD16$^-$CD49a$^+$CD39$^+$TIGIT$^+$-positive dNK cell subset-derived exosome | 11.62 | 13.26 | p < 0.05 |

Example 9

Effect of the Exosomes Derived from dNK Cells and dNK Cell Subsets on Helper T Cells The para-aortic lymph nodes were collected from the mice in the control group, the stress group, the control exosome group, and the NK cell-derived exosome treatment groups in Example 8, and the Foxp3-positive helper T cell levels in the lymph nodes were detected. The collection method and detection method could be seen in the literature (Kim B J, et al. Proceedings of the National Academy of Sciences, 2015, 112 (5): 1559-1564). Results showed that the treatment with the exosomes derived from dNK cells and dNK cell subsets could effectively increase the Foxp3-positive helper T cell level (Table 9).

TABLE 9

Foxp3% expression analysis for mice in each group

| Group | Percentage of Foxp3-positive Treg cells | SD | p value (relative to stress + control cells) |
|---|---|---|---|
| Blank control group | 42.85 | 5.78 | |
| Stress + control exosome | 8.39 | 0.80 | |
| CD56$^{bright}$CD16$^-$CD49a$^+$-positive dNK cell-derived exosome | 35.63 | 3.11 | p < 0.05 |
| CD56$^{bright}$CD16$^-$CD49a$^+$CD39$^+$-positive dNK cell subset-derived exosome | 28.46 | 1.51 | p < 0.05 |
| CD56$^{bright}$CD16$^-$CD49a$^+$CD27$^+$-positive dNK cell subset-derived exosome | 21.15 | 2.22 | p < 0.05 |
| CD56$^{bright}$CD16$^-$CD49a$^+$CD160$^+$-positive dNK cell subset-derived exosome | 30.93 | 4.97 | p < 0.05 |
| CD56$^{bright}$CD16$^-$CD49a$^+$TIGIT$^+$-positive dNK cell subset-derived exosome | 32.34 | 3.08 | p < 0.05 |
| CD56$^{bright}$CD16$^-$CD49a$^+$CD39$^+$TIGIT$^+$-positive dNK cell subset-derived exosome | 28.72 | 3.28 | p < 0.05 |

Example 10

Treatment of Mouse Endometrial Injury Models with the Exosomes Derived from dNK Cells and dNK Cell Subsets Establishment of animal endometrial injury models (C57 mice): 8-week-old female mice were divided into groups, each with 10 mice, and the double (infection+mechanical) damage method was used to establish the endometrial injury models. Specifically, the mice were anesthetized, a longitudinal incision of about 2 cm in the middle of the lower abdomen was provided to make a 0.5 cm longitudinal incision at a lower part ⅓ from the middle of the uterus; then an endometrial curette was used to curette the middle and upper segments of the uterine cavity; when the concave-convex feeling disappeared and the walls showed the roughness touch, the curettage was stopped; lipopolysaccharide cotton threads were left in the uterine cavity after curettage, and the abdominal incision was sutured; and the lipopolysaccharide cotton threads were taken out 48 h later. After the modeling was completed, the following groups were set: a blank control group (sham operation group); a group injected only with normal saline (NS) (model); model+ control exosome; and NK cell-derived exosome treatment groups. The treatment groups were intravenously administered with the exosomes derived from dNK cells and dNK cell subsets of the present disclosure (150 μg/mouse) once every 3 days, with a total of 3 administrations. The female mice were mated with male mice after 3 estrous cycles. 1 month later, samples were collected for HE staining and Masson staining to evaluate the function of the endometrial tissue. 3 months later, pregnancy results were evaluated for the mice. Results: The histological function evaluation 1 month after the operation showed that, compared with the control group, the groups administered with the exosomes derived from dNK cells and dNK cell subsets had a significantly-reduced fibrosis degree; and compared with the control group, the exosome treatment groups had a larger number of secretory glands. The evaluation of pregnancy results showed that the groups administered with the exosomes derived from dNK cells and dNK cell subsets had a conception rate higher than that of the control exosome group. The results were shown in Table 10.

TABLE 10

Pregnancy result analysis of mice in each group

| Group | Conception rate | p value (relative to control cells) |
|---|---|---|
| Blank control group | 100% | |
| Model group | 20% | |
| Model group + control exosome | 20% | |
| $CD56^{bright}CD16^-CD49a^+$-positive dNK cell-derived exosome | 50% | p < 0.05 |
| $CD56^{bright}CD16^-CD49a^+CD39^+$-positive dNK cell subset-derived exosome | 60% | p < 0.05 |
| $CD56^{bright}CD16^-CD49a^+CD27^+$-positive dNK cell subset-derived exosome | 70% | p < 0.05 |
| $CD56^{bright}CD16^-CD49a^+CD160^+$-positive dNK cell subset-derived exosome | 60% | p < 0.05 |
| $CD56^{bright}CD16^-CD49a^+TIGIT^+$-positive dNK cell subset-derived exosome | 70% | p < 0.05 |
| $CD56^{bright}CD16^-CD49a^+CD39^+TIGIT^+$-positive dNK cell subset-derived exosome | 60% | p < 0.05 |

Example 11

Effect of the Exosomes on Fertilized Eggs

C57BL/6J female mice (21 to 27 weeks old, body weight: 20.0 g to 24.5 g) were used to collect fertilized eggs. C57BL/6J male mice (32 to 38 weeks old, body weight: 31.0 g to 35.5 g) were used for mating. According to the conventional method of inducing excessive ovulation, 5 U (unit) of equine chorionic gonadotropin (eCG) was administered intraperitoneally to each female mouse, and 45 h to 48 h later, 5 U (unit) of human chorionic gonadotropin (HCG) was administered intraperitoneally to each female mouse. Each female mouse was mated with each of the above-mentioned male mice immediately after the administration of HCG.

The next day, it was determined whether the female mice after mating had a milky-white resinous vaginal plug, and the fallopian tubes were collected from female mice confirmed to have the vaginal plug. The collected fallopian tubes were statically placed in NS (0.9% (w/v) NaCl) for about 15 min and then transferred into an M16 medium added with about 300 µg/mL hyaluronidase (manufactured by Sigma-Aldrich) to remove cumulus cells. The fallopian tubes were cut, and fertilized eggs were taken out and statically incubated in a $CO_2$ incubator for 5 min to 10 min at 37° C. Then the fertilized eggs obtained after cumulus cells were removed were recovered, and washed with an M16 medium without hyaluronidase to remove the hyaluronidase. The fertilized eggs obtained after cumulus cells were removed were statically placed in a $CO_2$ incubator at 37° C.

In addition, drops were made with 100 µL of M16 medium in a 35 mm petri dish, and the drops were overlaid with mineral oil (produced by Sigma-Aldrich), and added with the exosomes derived from dNK cells and dNK cell subsets and the control exosome in Example 3, with a mass-volume ratio of 0.02%. The petri dish was statically placed in a $CO_2$ incubator at 37° C. 30 of the fertilized eggs obtained after cumulus cells were removed were transferred on the drops, and cultivated in vitro at 37° C. in a $CO_2$ incubator.

24 h, 48 h, 72 h, and 96 h after the beginning of in vitro cultivation in the drops (0 h), the developmental stage of each embryo was observed through a stereoscopic microscope, and the number and development rate of embryos developing normally were calculated. Specifically, for embryos developing normally at each stage, 24 h after the beginning of cultivation, the number of eggs at the 2-cell stage was calculated; 48 h after the beginning of cultivation, the number of eggs at each of the 3-cell stage, 4-cell stage, and 8-cell stage was calculated; 72 h after the beginning of cultivation, the numbers of morulas and blastocysts were calculated; and 96 h after the beginning of cultivation, the number of blastocysts was calculated. The number of embryos at each stage was recorded in Table 11, and the development rate (the number of fertilized eggs at 0 h was counted as 100%) was shown in Table 12. For the evaluation of development rate, with the number of fertilized eggs (at 0 h) as 100%, and a proportion of embryos developing normally was calculated at 24 h, 48 h, 72 h, and 96 h, which was the normal development rate. In addition, due to natural mating, the recovered fertilized eggs (at 0 h) included some unfertilized eggs, and even when a fertilized egg colony (at 0 h) recovered in the same experiment was allocated to fertilized egg colonies (at 0 h) under different conditions, the unfertilized egg content may also change occasionally. A development rate was also calculated with the number of embryos at the 2-cell stage 24 h after fertilization as 100%, and the calculation was conducted to exclude the influence of the unfertilized egg content that accidentally changed among condition groups. That is, in order to calculate the development rate based on the number of eggs that had actually started embryonic development, the number of eggs at the 2-cell stage 24 h after fertilization was set to 100%, and the development rate in this case was shown in Table 13. The statistical analysis of each result was conducted by chi-square test, and there were statistical significant differences at p<0.05 (*) and p<0.01 (**). Since the control exosome relatively reduced the embryonic development, statistical comparison was conducted relative to the medium group without any exosome.

TABLE 11

Number of developing embryos in each group

| Group | 0 h | 24 h | 48 h | 72 h | 96 h |
|---|---|---|---|---|---|
| Only medium | 30 | 18 | 18 | 10 | 2 |
| Control exosome | 30 | 17 | 17 | 6 | 0 |
| $CD56^{bright}CD16^-CD49a^+$-positive dNK cell-derived exosome | 30 | 23 | 21 | 15 | 15 |
| $CD56^{bright}CD16^-CD49a^+CD39^+$-positive dNK cell subset-derived exosome | 30 | 23 | 20 | 15 | 14 |

TABLE 11-continued

Number of developing embryos in each group

| Group | 0 h | 24 h | 48 h | 72 h | 96 h |
|---|---|---|---|---|---|
| CD56$^{bright}$CD16$^-$CD49a$^+$CD27$^+$-positive dNK cell subset-derived exosome | 30 | 24 | 20 | 15 | 14 |
| CD56$^{bright}$CD16$^-$CD49a$^+$CD160$^+$-positive dNK cell subset-derived exosome | 30 | 24 | 21 | 15 | 14 |
| CD56$^{bright}$CD16$^-$CD49a$^+$TIGIT$^+$-positive dNK cell subset-derived exosome | 30 | 24 | 21 | 15 | 15 |
| CD56$^{bright}$CD16$^-$CD49a$^+$CD39$^+$TIGIT$^+$-positive dNK cell subset-derived exosome | 30 | 23 | 21 | 15 | 15 |

TABLE 12

Development rate of each group (%) calculated with the number of fertilized eggs at 0 h as 100%

| Group | 0 h | 24 h | 48 h | 72 h | 96 h |
|---|---|---|---|---|---|
| Only medium | 100.00 | 60.00 | 60.00 | 33.33 | 6.67 |
| Control exosome | 100.00 | 56.67 | 56.67 | 20.00 | 0.00* |
| CD56$^{bright}$CD16$^-$CD49a$^+$-positive dNK cell-derived exosome | 100.00 | 76.67 | 70.00 | 50.00* | 50.00** |
| CD56$^{bright}$CD16$^-$CD49a$^+$CD39$^+$-positive dNK cell subset-derived exosome | 100.00 | 76.67 | 66.67 | 50.00* | 46.67** |
| CD56$^{bright}$CD16$^-$CD49a$^+$CD27$^+$-positive dNK cell subset-derived exosome | 100.00 | 80.00 | 66.67 | 50.00* | 46.67** |
| CD56$^{bright}$CD16$^-$CD49a$^+$CD160$^+$-positive dNK cell subset-derived exosome | 100.00 | 80.00 | 70.00 | 50.00* | 46.67** |
| CD56$^{bright}$CD16$^-$CD49a$^+$TIGIT$^+$-positive dNK cell subset-derived exosome | 100.00 | 80.00 | 70.00 | 50.00* | 50.00** |
| CD56$^{bright}$CD16$^-$CD49a$^+$CD39$^+$TIGIT$^+$-positive dNK cell subset-derived exosome | 100.00 | 76.67 | 70.00 | 50.00* | 50.00** |

TABLE 13

Development rate of each group (%) calculated with the number of fertilized eggs at 24 h as 100%

| Group | 24 h | 48 h | 72 h | 96 h |
|---|---|---|---|---|
| Only medium | 100.00 | 100.00 | 55.56 | 11.11 |
| Control exosome | 100.00 | 100.00 | 35.29 | 0.00* |
| CD56$^{bright}$CD16$^-$CD49a$^+$-positive dNK cell-derived exosome | 100.00 | 91.30 | 65.22 | 65.22** |
| CD56$^{bright}$CD16$^-$CD49a$^+$CD39$^+$-positive dNK cell subset-derived exosome | 100.00 | 86.96 | 65.22 | 60.87** |
| CD56$^{bright}$CD16$^-$CD49a$^+$CD27$^+$-positive dNK cell subset-derived exosome | 100.00 | 83.33 | 62.50 | 58.33** |
| CD56$^{bright}$CD16$^-$CD49a$^+$CD160$^+$-positive dNK cell subset-derived exosome | 100.00 | 87.50 | 62.50 | 58.33** |
| CD56$^{bright}$CD16$^-$CD49a$^+$TIGIT$^+$-positive dNK cell subset-derived exosome | 100.00 | 87.50 | 62.50 | 62.50** |
| CD56$^{bright}$CD16$^-$CD49a$^+$CD39$^+$TIGIT$^+$-positive dNK cell subset-derived exosome | 100.00 | 91.30 | 65.22 | 65.22** |

(chi-square test vs only medium group, **: $p<0.01$, and *: $p<0.05$)

Results showed that, when the number of fertilized eggs at 0 h was counted as 100%, compared with the control without any exosome, each group treated with an exosome derived from dNK cells or a dNK cell subset showed an increased development rate. The control exosome may have some cytotoxicity because it was derived from peripheral blood NK cells.

Example 12

Effect of the Exosomes on In Vitro Fertilized Eggs

5 U (units) of eCG was administered intraperitoneally to C57BL/6J female mice (3.9 to 4.0 weeks old), and 45 h to 48 h later, 5 U (units) of HCG (produced by ASKA Pharmaceutical Co., Ltd.) was administered intraperitoneally to induce excessive ovulation. 15 h after the administration of HCG, the laparotomy was conducted to collect fallopian tubes. In mineral oil, enlarged parts of the fallopian tubes were cut with a dissecting needle, and eggs were recovered into drops of mHTF medium. Sperm were recovered from the epididymal tail of C57BL/6J male mice, and then cultivated in mHTF medium at 37° C. and 5% $CO_2$ for 40 min to 1 h to achieve sperm capacitation. 2 μl to 4 μl of the sperm-containing mHTF medium was added to the medium drops with the collected eggs.

Fertilization was conducted at 37° C. and 5% $CO_2$. 4 h to 6 h after fertilization, fertilized eggs were washed with KSOM medium to remove cumulus cells and sperm. The fertilized eggs were temporarily cultivated in a 37° C. and 5% $CO_2$ incubator with KSOM or mWM medium until all fertilized eggs were recovered.

Drops were formed with 100 μl of medium (which were overlaid with mineral oil (produced by Sigma-Aldrich), and some were added with the exosomes derived from dNK cells and dNK cell subsets and the control exosome described in Example 3 at a final concentration of 0.02%. 25 fertilized eggs were transferred into each drop, with 200 fertilized eggs for each treatment group. Then the fertilized eggs were cultivated. The number of embryos at the 2-cell stage 24 h after egg recovery and the number of blastocysts 96 h after egg recovery were determined. In addition, since the development of fertilized eggs obtained from in vitro fertilization would be slightly delayed, the number of blastocysts 120 h after the egg recovery was also determined. The number of embryos at the 2-cell stage 24 h after fertilization was counted as 100%, and on this basis, the embryo development rate at each cultivation time was calculated. Results were shown in Table 14.

TABLE 14

Number of developing embryos in each group

| Group | 0 h | 24 h | 48 h | 72 h | 96 h | 120 h |
|---|---|---|---|---|---|---|
| Only medium | 200 | 144 | 101 | 99 | 91 | 90 |
| Control exosome | 200 | 135 | 111 | 80 | 60 | 55 |
| $CD56^{bright}CD16^-CD49a^+$-positive dNK cell-derived exosome | 200 | 156 | 144 | 143 | 140 | 139 |
| $CD56^{bright}CD16^-CD49a^+CD39^+$-positive dNK cell subset-derived exosome | 200 | 150 | 138 | 135 | 130 | 129 |
| $CD56^{bright}CD16^-CD49a^+CD27^+$-positive dNK cell subset-derived exosome | 200 | 145 | 131 | 129 | 125 | 125 |
| $CD56^{bright}CD16^-CD49a^+CD160^+$-positive dNK cell subset-derived exosome | 200 | 140 | 135 | 133 | 130 | 129 |
| $CD56^{bright}CD16^-CD49a^+TIGIT^+$-positive dNK cell subset-derived exosome | 200 | 138 | 125 | 120 | 120 | 120 |
| $CD56^{bright}CD16^-CD49a^+CD39^+TIGIT^+$-positive dNK cell subset-derived exosome | 200 | 141 | 130 | 122 | 121 | 121 |

TABLE 15

Development rate of each group (%) calculated with the number of fertilized eggs at 24 h as 100%

| Group | 24 h | 48 h | 72 h | 96 h | 120 h |
|---|---|---|---|---|---|
| Only medium | 100.00 | 72.00 | 50.50 | 49.50 | 45.50 |
| Control exosome | 100.00 | 67.50 | 55.50 | 40.00 | 30.00* |
| $CD56^{bright}CD16^-CD49a^+$-positive dNK cell-derived exosome | 100.00 | 78.00 | 72.00 | 71.50 | 70.00* |
| $CD56^{bright}CD16^-CD49a^+CD39^+$-positive dNK cell subset-derived exosome | 100.00 | 75.00 | 69.00 | 67.50 | 65.00* |
| $CD56^{bright}CD16^-CD49a^+CD27^+$-positive dNK cell subset-derived exosome | 100.00 | 72.50 | 65.50 | 64.50 | 62.50* |
| $CD56^{bright}CD16^-CD49a^+CD160^+$-positive dNK cell subset-derived exosome | 100.00 | 70.00 | 67.50 | 66.50 | 65.00* |
| $CD56^{bright}CD16^-CD49a^+TIGIT^+$-positive dNK cell subset-derived exosome | 100.00 | 69.00 | 62.50 | 60.00 | 60.00* |
| $CD56^{bright}CD16^-CD49a^+CD39^+TIGIT^+$-positive dNK cell subset-derived exosome | 100.00 | 70.50 | 65.00 | 61.00 | 60.50* |

(chi-square test vs only medium group, **: $p<0.01$, and *: $p<0.05$)

Results showed that, when the number of fertilized eggs at 24 h was counted as 100%, compared with the control without any exosome, each group treated with a dNK cell-derived exosome showed an increased development rate. The control exosome may have some cytotoxicity because it was derived from peripheral blood NK cells.

Example 13

Effect of the Exosomes on In Vitro Fertilized Egg Transfer

Embryos at the blastocyst stage in each group of Example 12 were transferred. Recipient mice were C57BL/6J female mice at 6 to 10 weeks old. The female mice were mated with vasectomized C57BL/6J male mice on the day before egg transfer, and on the next day, individuals with a vaginal plug were confirmed. General anesthesia was conducted with somnopentyl, and the back was incised to expose the uterus. The uterus was fixed with forceps, a 30 G injection needle was used to open a hole at the oviduct junction, and a glass capillary adsorbing a blastocyst was inserted to transfer the embryo into the uterus. After the transfer, the uterus was carefully put back into the body, and the retroperitoneum and skin were sutured. The blastocysts obtained from mice in each group were transferred into a corresponding recipient mice, separately. With the second day after egg collection being set as day 1, the caesarean section was conducted on day 19. The recipient mice were euthanized and laparotomized, and the uteruses were collected and the fetuses were taken out. An implantation rate was calculated according to the following formula: the number of implantation marks/the number of embryo transfers (Table 16), and a birth rate was calculated according to the following formula: the number of fetuses/the number of embryo transfers (Table 17).

TABLE 16

Implantation rate of each group

| Group | Number of implantation marks | Number of embryo transfers | Implantation rate (%) |
|---|---|---|---|
| Only medium | 42 | 90 | 46.67 |
| Control exosome | 6 | 55 | 10.91 |
| $CD56^{bright}CD16^-CD49a^+$-positive dNK cell-derived exosome | 123 | 139 | 88.49* |
| $CD56^{bright}CD16^-CD49a^+CD39^+$-positive dNK cell subset-derived exosome | 121 | 129 | 93.80** |
| $CD56^{bright}CD16^-CD49a^+CD27^+$-positive dNK cell subset-derived exosome | 115 | 125 | 92.00* |
| $CD56^{bright}CD16^-CD49a^+CD160^+$-positive dNK cell subset-derived exosome | 110 | 129 | 85.27* |
| $CD56^{bright}CD16^-CD49a^+TIGIT^+$-positive dNK cell subset-derived exosome | 98 | 120 | 81.67* |
| $CD56^{bright}CD16^-CD49a^+CD39^+TIGIT^+$-positive dNK cell subset-derived exosome | 105 | 121 | 86.78* |

(chi-square test vs only medium group, **: $p<0.01$, and *: $p<0.05$)

TABLE 17

Birth rate of each group

| Group | Number of fetuses | Number of embryo transfers | Birth rate (%) |
|---|---|---|---|
| Only medium | 40 | 90 | 44.44 |
| Control exosome | 2 | 55 | 3.64 |
| $CD56^{bright}CD16^-CD49a^+$-positive dNK cell-derived exosome | 122 | 139 | 87.77* |
| $CD56^{bright}CD16^-CD49a^+CD39^+$-positive dNK cell subset-derived exosome | 119 | 129 | 92.25** |
| $CD56^{bright}CD16^-CD49a^+CD27^+$-positive dNK cell subset-derived exosome | 110 | 125 | 88.00* |
| $CD56^{bright}CD16^-CD49a^+CD160^+$-positive dNK cell subset-derived exosome | 97 | 129 | 75.19* |
| $CD56^{bright}CD16^-CD49a^+TIGIT^+$-positive dNK cell subset-derived exosome | 92 | 120 | 76.67* |
| $CD56^{bright}CD16^-CD49a^+CD39^+TIGIT^+$-positive dNK cell subset-derived exosome | 101 | 121 | 83.47* |

(chi-square test vs only medium group, **: $p<0.01$, and *: $p<0.05$)

Results showed that, compared with the control without any exosome, each group treated with a dNK cell-derived exosome showed an increased implantation rate and an increased birth rate. The control exosome may have some cytotoxicity because it was derived from peripheral blood NK cells.

The basic principles, main features, and advantages of the present disclosure are shown and described above. It should be understood by those skilled in the art that, the present disclosure is not limited by the above examples, and the above examples and the description only illustrate the principle of the present disclosure. Various changes and modifications may be made to the present disclosure without departing from the spirit and scope of the present disclosure, and such changes and modifications all fall within the claimed scope of the present disclosure. The protection scope of the present disclosure is defined by the appended claims and equivalents thereof.

What is claimed is:

1. A method of preparing a drug and an auxiliary therapeutic agent for infertility-related diseases, comprising the step of using an exosome derived from decidual natural killer (dNK) cells or a dNK cell subset.

2. The method according to claim 1, wherein
the dNK cells have a surface marker of $CD56^{bright}CD16^-CD49a^+$, and the dNK cell subset refers to dNK cells with a surface marker, and the surface marker is at least one selected from the group consisting of $CD39^+$, $CD27^+$, $CD160^+$, and $TIGIT^+$.

3. The method according to claim 1, wherein
the drug for treating the infertility-related diseases is a drug for treating endometrial growth disorder-related diseases or a drug for treating maternal-fetal immune tolerance disorder-related diseases; and
the auxiliary therapeutic agent is an agent composition for improving a normal development rate of fertilized eggs.

4. The method according to claim 3, wherein
the drug for treating the endometrial growth disorder-related diseases is at least one selected from the group consisting of a drug for promoting increase of endometrial thickness, a drug for enhancing endometrial cell viability, a drug for reducing endometrial cell damage, a drug for promoting vascular endothelial growth factor (VEGF) expression, and a drug for maintaining stemness and stimulating proliferation of endometrial stromal cells;
the drug for treating the maternal-fetal immune tolerance disorder-related diseases is at least one selected from the group consisting of a drug for maintaining or enhancing immune tolerance, a drug for treating spontaneous abortion, and a drug for increasing a helper T cell level; and
the agent composition for improving the normal development rate of fertilized eggs is an agent for promoting the development and maturation of fertilized eggs or blastocysts, or a fertilized egg medium or in vitro fertilization medium comprising the exosome.

5. The method according to claim 1, wherein a preparation method of the exosome comprises:
A) isolation of the dNK cells and the dNK cell subset:
subjecting a decidual tissue to enzymatic digestion to obtain a cell suspension, isolating lymphocytes through density gradient centrifugation, and isolating the dNK cells with a marker of $CD56^{bright}CD16^-CD49a^+$ from the lymphocytes using anti-CD56 antibody, anti-CD16 antibody, and anti-CD49a antibody; and isolating the dNK cell subset using anti-CD39 antibody, anti-CD27 antibody, anti-CD160 antibody, and anti-TIGIT antibody;
B) NK cell cultivation in vitro:
transferring the dNK cells or the dNK cell subset to CTS AIM-V medium, 1640 medium, or DMEM medium free of serum, and cultivating the dNK cells or the dNK cell subset at 37° C. and 5% $CO_2$ for 24 h to 96 h;
C) isolation of the exosome:
filtering the CTS AIM-V medium, the 1640 medium, or the DMEM medium in step B through a filter membrane to obtain a filtrate, and subjecting the filtrate successively to centrifugation at 4° C. and 1,000 g for 10 min, centrifugation at 4° C. and 2,000 g for 20 min, centrifugation at 4° C. and 10,000 g for 30 min, and centrifugation at 110,000 g for 90 min to obtain a first mixture; discarding a supernatant of the first mixture to obtain a first precipitate, and resuspending the first precipitate with phosphate buffered saline (PBS) to obtain a first suspension; subjecting the first suspension once again to centrifugation at 110,000 g for 90 min to obtain a second mixture, discarding a supernatant of the second mixture to obtain a second precipitate, and resuspending the second precipitate with a small amount of PBS to obtain a second suspension; and filtering the second suspension through a 0.45 μm filter membrane to obtain the exosome.

6. The method according to claim 1, wherein
the drug is a pharmaceutical composition having the exosome as the only active ingredient or comprising the exosome; and
the auxiliary therapeutic agent is an agent composition comprising the exosome.

7. The method according to claim 6, wherein
the pharmaceutical composition is a tablet, a pill, a powder, an injection, a tincture, a solution, an extract, an ointment, a film, a suppository, an effervescent tablet, a gel, a mucosal absorption enhancer, or an intrauterine drug delivery system.

8. The method according to claim 2, wherein a preparation method of the exosome comprises:
A) isolation of the dNK cells and the dNK cell subset:
subjecting a decidual tissue to enzymatic digestion to obtain a cell suspension, isolating lymphocytes through density gradient centrifugation, and isolating the dNK cells with a marker of $CD56^{bright}CD16^-CD49a^+$ from the lymphocytes using anti-CD56 antibody, anti-CD16 antibody, and anti-CD49a antibody; and isolating the dNK cell subset using anti-CD39 antibody, anti-CD27 antibody, anti-CD160 antibody, and anti-TIGIT antibody;
B) NK cell cultivation in vitro:
transferring the dNK cells or the dNK cell subset to CTS AIM-V medium, 1640 medium, or DMEM medium free of serum, and cultivating the dNK cells or the dNK cell subset at 37° C. and 5% $CO_2$ for 24 h to 96 h;
C) isolation of the exosome:
filtering the CTS AIM-V medium, the 1640 medium, or the DMEM medium in step B through a filter membrane to obtain a filtrate, and subjecting the filtrate successively to centrifugation at 4° C. and 1,000 g for 10 min, centrifugation at 4° C. and 2,000 g for 20 min, centrifugation at 4° C. and 10,000 g for 30 min, and centrifugation at 110,000 g for 90 min to obtain a first mixture; discarding a supernatant of the first mixture to obtain a first precipitate, and resuspending the first precipitate with phosphate buffered saline (PBS) to obtain a first suspension; subjecting the first suspension once again to centrifugation at 110,000 g for 90 min to obtain a second mixture, discarding a supernatant of the second mixture to obtain a second precipitate, and resuspending the second precipitate with a small amount of PBS to obtain a second suspension; and filtering the second suspension through a 0.45 μm filter membrane to obtain the exosome.

9. The method according to claim 3, wherein a preparation method of the exosome comprises:
A) isolation of the dNK cells and the dNK cell subset:
subjecting a decidual tissue to enzymatic digestion to obtain a cell suspension, isolating lymphocytes through density gradient centrifugation, and isolating the dNK cells with a marker of $CD56^{bright}CD16^-CD49a^+$ from the lymphocytes using anti-CD56 antibody, anti-CD16 antibody, and anti-CD49a antibody; and isolating the dNK cell subset using anti-CD39 antibody, anti-CD27 antibody, anti-CD160 antibody, and anti-TIGIT antibody;
B) NK cell cultivation in vitro:
transferring the dNK cells or the dNK cell subset to CTS AIM-V medium, 1640 medium, or DMEM medium free of serum, and cultivating the dNK cells or the dNK cell subset at 37° C. and 5% $CO_2$ for 24 h to 96 h;
C) isolation of the exosome:
filtering the CTS AIM-V medium, the 1640 medium, or the DMEM medium in step B through a filter membrane to obtain a filtrate, and subjecting the filtrate successively to centrifugation at 4° C. and 1,000 g for 10 min, centrifugation at 4° C. and 2,000 g for 20 min, centrifugation at 4° C. and 10,000 g for 30 min, and centrifugation at 110,000 g for 90 min to obtain a first mixture; discarding a supernatant of the first mixture to obtain a first precipitate, and resuspending the first precipitate with phosphate buffered saline (PBS) to obtain a first suspension; subjecting the first suspension once again to centrifugation at 110,000 g for 90 min to obtain a second mixture, discarding a supernatant of the second mixture to obtain a second precipitate, and resuspending the second precipitate with a small amount of PBS to obtain a second suspension; and filtering the second suspension through a 0.45 μm filter membrane to obtain the exosome.

10. The method according to claim 4, wherein a preparation method of the exosome comprises:
A) isolation of the dNK cells and the dNK cell subset;
subjecting a decidual tissue to enzymatic digestion to obtain a cell suspension, isolating lymphocytes through density gradient centrifugation, and isolating the dNK cells with a marker of $CD56^{bright}CD16^-CD49a^+$ from the lymphocytes using anti-CD56 antibody, anti-CD16 antibody, and anti-CD49a antibody; and isolating the dNK cell subset using anti-CD39 antibody, anti-CD27 antibody, anti-CD160 antibody, and anti-TIGIT antibody;
B) NK cell cultivation in vitro;
transferring the dNK cells or the dNK cell subset to CTS AIM-V medium, 1640 medium, or DMEM medium free of serum, and cultivating the dNK cells or the dNK cell subset at 37° C. and 5% $CO_2$ for 24 h to 96 h;
C) isolation of the exosome:
filtering the CTS AIM-V medium, the 1640 medium, or the DMEM medium in step B through a filter membrane to obtain a filtrate, and subjecting the filtrate successively to centrifugation at 4° C. and 1,000 g for 10 min, centrifugation at 4° C. and 2,000 g for 20 min, centrifugation at 4° C. and 10,000 g for 30 min, and centrifugation at 110,000 g for 90 min to obtain a first mixture; discarding a supernatant of the first mixture to obtain a first precipitate, and resuspending the first precipitate with phosphate buffered saline (PBS) to obtain a first suspension; subjecting the first suspension once again to centrifugation at 110,000 g for 90 min to obtain a second mixture, discarding a supernatant of the second mixture to obtain a second precipitate, and resuspending the second precipitate with a small amount of PBS to obtain a second suspension; and filtering the second suspension through a 0.45 μm filter membrane to obtain the exosome.

* * * * *